United States Patent [19]

Ishikawa et al.

[11] Patent Number: 4,482,729

[45] Date of Patent: Nov. 13, 1984

[54] FLUOROALKYL SILYL KETENE ACETALS AND A PROCESS FOR PREPARING THE SAME

[75] Inventors: Nobuo Ishikawa; Takeshi Nakai, both of Yokohama, Japan

[73] Assignee: Daikin Kogyo Co., Ltd., Osaka, Japan

[21] Appl. No.: 586,947

[22] Filed: Mar. 4, 1984

[51] Int. Cl.³ .............................................. C07F 7/08
[52] U.S. Cl. ................................................. 556/446
[58] Field of Search ...................................... 556/446

[56] References Cited

U.S. PATENT DOCUMENTS

3,655,555  4/1972  Rossmy et al. ................. 556/446 X

FOREIGN PATENT DOCUMENTS

| 0005924 | 1/1979 | Japan | 556/446 |
| 0086190 | 7/1981 | Japan | 556/446 |
| 0207912 | 2/1968 | U.S.S.R. | 556/446 |
| 0717057 | 2/1980 | U.S.S.R. | 556/446 |

*Primary Examiner*—Paul F. Shaver
*Attorney, Agent, or Firm*—Armstrong, Nikaido, Marmelstein & Kubovcik

[57] ABSTRACT

A fluoroalkyl silyl ketene acetal of the formula

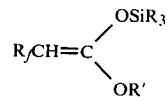

wherein $R_f$ is a fluoroalkyl group, and R and R' are the same or different and each is an alkyl group, which is prepared by reacting or fluorinated carboxylic acid of the formula

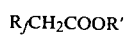

wherein $R_f$ and R' are respectively the same as defined above with a silylating agent represented by a formula

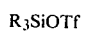

wherein Tf represents a trifluoromethane sulfonyl group and R is the same as defined above.

6 Claims, No Drawings

FLUOROALKYL SILYL KETENE ACETALS AND A PROCESS FOR PREPARING THE SAME

BACKGROUND OF THE INVENTION

1. Field of the Invention

The present invention relates to a fluoroalkyl silyl ketene acetal, that is useful as the intermediate for the synthesis of physiologically active substances having a fluoroalkyl substituent, and a process for preparing the same.

2. Description of the Prior Art

A group of compounds having a $CF_3$ substituent have been noticed for their physiological activities. A possible method of synthesis of such $CF_3$ containing compounds is to form various carbon-carbon bonds to a synthetic block having a $CF_3$ substituent. However, there are only very few disclosures of such method, for example, α-trifluoromethyl malonic acid ester published at the 8th Fluorine Chemistry Discussion in Japan(1982).

OBJECTS AND SUMMARY OF THE INVENTION

The present authors thus noticed 3,3,3-trifluoropropionic acid esters as such synthetic block and succeeded to synthesized their equivalent in synthesis, namely, their ester enolate form or trifluoromethylsilyketene acetals, which has led to the present invention.

Accordingly it is an object of the present invention to provide a fluoroaokyl silyl ketene acetal represented by a general formula

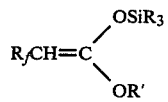

wherein $R_f$ represents a fluoroalkyl group, and R and R' are the same or different and each represents an alkyl group.

It is another object of the invention to provide a process for preparing said fluoroalkyl silyl ketene acetal, comprising reacting a fluorinated carboxylic acid ester represented by a formula

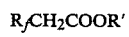

wherein $R_f$ and R' are respectively the same as defined above with a silylating agent represented by a formula

wherein Tf represents a trifluoromethanesulfonyl group and R represents the same as defined above.

In the present invention, for $R_f$ in the above formulas, a group of 1 to 10 carbon atoms may be used and for each of R and R' therein, an alkyl group of 1 to 10 carbon atoms may be used. Examples of such group are $-CF_3$, $-C_2F_5$ and $-C_3F_7$ while examples of such alkyl group are $-CH_3$, $-C_2H_5$ and $-C_3H_7$.

In the process of the invention, the solvent used is preferably an organic solvent, such as diethyl ether or dichloromethane.

Other objects and advantages of the invention will become apparent from the following description of embodiments.

DESCRIPTION OF THE PREFERRED EMBODIMENTS

When trimethylsilyltriflate ($Me_3SiOTf$) has been used in synthesis of an enolate equivalent trifluoromethysilylketeneactal 2 from 3,3,3-trifluoropropionic acid ester 1 according to the following reaction, the target silyl ketene acetal 2 has been produced in a high yield (for example, 92% from $^{19}F$ NMR data):

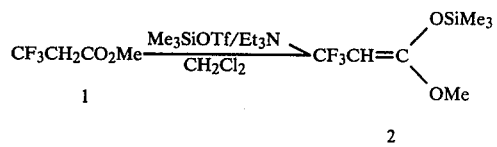

Such a high yield in the synthesis of silyl ketene acetal 2 is noteworthy since if an ordinary ester having no trifluoro -methyl group is used as the starting material, the $Me_3SiOTf/Et_3N$ reaction system gives a α-trimethylsilyl ester. In fact, it has been even confirmed that methyl propionate, if used, gives α-trimethylsilyl ester as the principal product. In contrast to that, it has been found that if an ester having a $CF_3$ group, which is highly electron attractive, at its α-position is used as the starting material as in the present invention, the reaction proceeds as mentioned above.

The chemical structure of acetal 2 was identified by $^1H$ NMR and $^{19}F$ NMR. It was confirmed that the ratio of geometric isomers was E:Z=1:4.

Further, from a finding that the acetal 2 as synthesized above could undergo the following reaction with various carbon's electron-seeking compounds (electrophilic reagents) under Lewis acidic condition, it has been revealed that this acetal can be used as a useful block for the synthesis of α-trifluoromethyl esters, etc.:

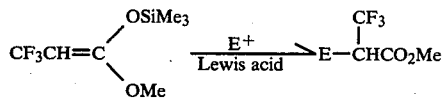

wherein E+ is an electrophilic reagent.

This reaction can be conducted with the reaction giving the actal 2 in situ, namely, without isolation. For example, when the acetal 2 has been reacted with propionic acid chloride ($CH_3CH_2COCl$) as follows, a corresponding α-trifluoromethyl-β-ketoester 4 has been and isolated at a yield of 54%.

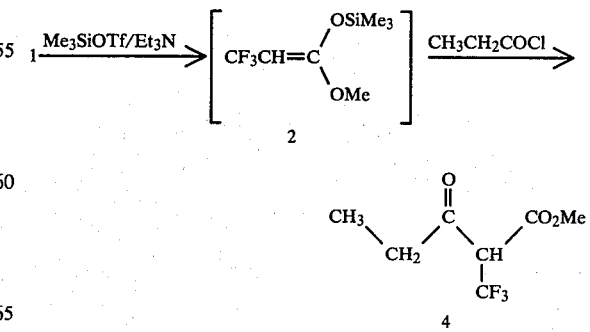

In addition to the above reaction, it has been found that when an aldol addition type reaction is applied to the acetal 2, α-trifluoromethylated carboxylic acid ester 5 can be formed as follows:

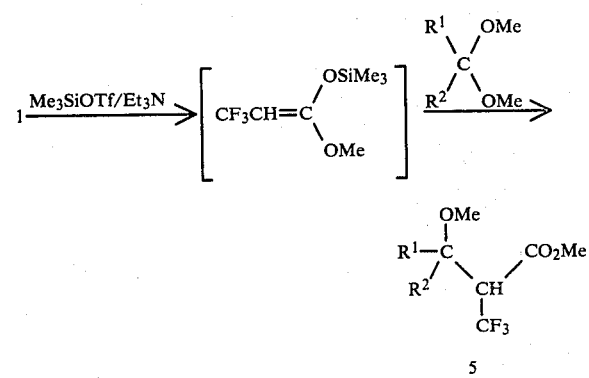

More specifically, when an aldol addition type reaction has been performed with acetals using the trimethyl silyl triflate (Me₃SiOTf) as catalysts, 1.2 equivalent of said triflate has been used relative to the ester 1 in consideration of the fact that the acetal 2 releases fluoride ions F⁻ readily. The actetal 2 thus produced is cooled down to −78° C. in situ and then various carbonyl substrates are added thereto for the addition reaction. The reaction completes in several hours giving the corresponding aldol adduct 5 in high yield. Aldol adduct compounds thus produced are listed in Table 1. Except for one example, namely in the case of sample 4, the reaction always showed only a low diastereo selectivity.

It is noted that the erythro form of the Sample 5 is equivalent to the trifluoro form of an intermediate used for the synthesis of antibiotics oudemansin. It is thus expected that trifluorooudemansin can be synthesized by the following reaction:

TABLE 1

| Sample | Electrophile | Reaction cond. | Product | Yield, % (diastereo selection ratio) |
|---|---|---|---|---|
| 1 | CH₃-C(OMe)(OMe)-CH₃ | −78° C. 6 h | MeO-C(CH₃)(CH₃)-CH(CF₃)-CO₂Me | 74 |
| 2 | CH₃-CH(OMe)(OMe) | −78° C. 6 h | MeO-CH(CH₃)-CH(CF₃)-CO₂Me | 81 (55:45) |
| 3 | Ph-CH(OMe)(OMe) | −78° C. 4.5 h | Ph-CH(OMe)-CH(CF₃)-CO₂Me | 89 (67:33) |
| 4 | (CH₃)₃C-C₆H₁₀-C(OMe)(OMe) | −78° C. 9 h | (CH₃)₃C-C₆H₁₀-C(OMe)(CO₂Me)-CH(CF₃) | 82 (100:0) |
| 5 | Ph-CH=CH-CH(OMe)(OMe) | −78° C. 5 h | Ph-CH=CH-CH(OMe)-CH(CF₃)-CO₂Me | 92 (55:45) |
| 6 | HC(OMe)₃ | −78° C. 5 h | MeO-CH(OMe)-CH(CF₃)-CO₂Me | 76 |

TABLE 1-continued

| Sample | Electrophile | Reaction cond. | Product | Yield, % (diastereo selection ratio) |
|---|---|---|---|---|
| 7 | PhCHO | −78° C. 5 h | Ph-CH(OH)-CH(CF₃)-CO₂Me | 93 (60:40) |

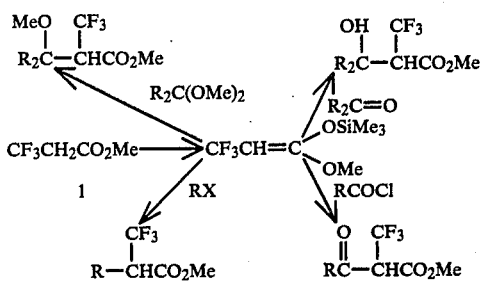

It has been confirmed that, as in the above case of Sample 7, the aldol addition reaction of acetal 2 and benzaldehyde gives the corresponding β-hydroxy-α-trifluoromethyl ester in high yield.

As mentioned above, the acetal 2 is useful as an intermediate for various processes of synthesis. This is summarized in the following diagram:

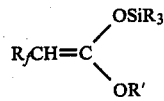

The invention will be more clearly understood with reference to the following examples.

EXAMPLE

Synthesis of TFPE:

Methyl 2-(trifluoromethyl)-3,3,3-trifluoroproionate. 200 ml of conc. sulfuric acid was added dropwisely to 232 g (1.0 mol) of octafluoroiso-butene-methanol adduct and the mixture was agitated overnight at room temperature. It was then poured over ice and the oily layer was separated, washed with water, saturated aqueous sodium bicarbonate solution and then water, and dried on magnesium sulfate. Purification by distillation gave methyl 2-(trifluoromethyl)-3,3,3-trifluoropropionate (184 g, 88%).

Its analysis gave the following data:
B.p.: 89°–90° C.,
$^{19}F$ NMR (neat): δ-12.5 (d, J=6.2 Hz).

Methyl 3,3,3-trifluoropropionate (TFPE). A solution of 150 g (1.5 mol) of potassium acetate in 500 ml of water was added dropwise to a solution of 105 g (0.5 mol) of methyl 2-(trifluoromethyl)-3,3,3-trifluoropropionate as above produced in 250 ml of water and the mixture was refluxed for 5 hours. After separation of the oily layer, extraction was made from the water layer that was left with use of methylene chloride and the solution of extracts and separated oily layer were joined and dried. After methylene chloride was removed by evaporation under atmospheric pressure, purification was made by distillation to give methyl 3,3,3-trifluoropropionate (TFPE) (54.07 g, 76%). Its analysis gave the following data:

B.p.: 95° to 95.5° C.,
IR (capillary film): 2970, 1760, 1440, 1230, 1120 cm$^{-1}$,
$^{1}H$ NMR (CCl₄): δ 3.13 (q, J=10.3 Hz, 2H), 3.77 (s, 3H),
$^{19}F$ NMR (neat): δ-12.7 (t, J=10.3 Hz), Synthesis of trifluoromethylsilylketene acetal:

1-(trimethylsiloxy)-1-methoxy-3,3,3-trifluoro-1-propene (E:Z=1:4). A solution of 0.71 g (5 mmol) of TFPE as above obtained in 3 ml of dry methylene chloride was added dropwise to a mixture of 1.00 ml (5.5 mmol) of trimethylsilyl triflate, 0.77 ml (5.5 mmol) of triethylamine and 3 ml of dry methylene chloride and the solution was agitated for 18 hours at room temperature. After a trap of −90° C. was attached, distillation was performed by flash evapoation at room temperature/2 mmHg to produce 1-(trimethylsiloxy)-1-methoxy-3,3,3-trifluoro-1-propene in methylene chloride (Yield: 86%). Its analysis gave the following data:

E form: $^{1}H$ NMR (CDCl₃): δ 0.32 (s, 9H), 3.67 (s, 3H), 3.90 (q, J=7.6 Hz, 1H), $^{19}F$ NMR (CDCl₃): δ −23.9 (d, J=7.6 Hz).

Z form: $^{1}H$ NMR (CDCl₃): δ 0.24 (s, 9H), 3.61 (s, 3H), 3.96 (q, J=7.1 Hz, 1H), $^{19}F$ NMR (CDCl₃): δ −24.2 (d, J=7.1 Hz).

It is noted that the yield was determined from $^{19}F$ NMR data obtained using fluorobenzene as the standard and the ratio of the E form to the Z form was also determined from $^{19}F$ NMR data.

What is claimed is:

1. A Fluoroalkyl silyl ketene acetal represented by a general formula $$R_fCH=C\begin{matrix}OSiR_3\\OR'\end{matrix}$$

wherein $R_f$ represents a fluoroalkyl group, and R and R' are the same or different and each represents an alkyl group.

2. An Acetal as claimed in claim 1 wherein said $R_f$ is a fluoroalkyl group of 1 to 10 carbon atoms.

3. An Acetal as claimed in claim 1 wherein R and R' are the same or different and each represents an alkyl group of 1 to 10 carbon atoms.

4. A process for preparing a fluoroalkyl silyl ketene acetal represented by a general formula $$R_f CH = C \begin{matrix} OSiR_3 \\ OR' \end{matrix}$$

wherein $R_f$ represents a fluoroalkyl group, and R and R' are the same or different and each represents an alkyl group, comprising reacting a fluorinated carboxylic acid ester represented by a formula $$R_f CH_2 COOR'$$

wherein $R_f$ and R' are respectively the same as defined above with a silylating agent represented by a formula $$R_3SiOTf$$

wherein Tf represents a trifluoromethane sulfonyl group and R is the same as defined above.

5. A process as claimed in claim 4 wherein $R_f$ is a fluoroalkyl group of 1 to 10 carbon atoms and R' is an alkyl group of 1 to 10 carbon atoms.

6. A process as claimed in claim 4 wherein R is an alkyl group of 1 to 10 carbon atoms.

* * * * *